United States Patent [19]

Percarpio

[11] 4,212,308
[45] Jul. 15, 1980

[54] PARALLEL-FLOW ONE-WAY BLOOD SAMPLING DEVICE

[75] Inventor: Edward P. Percarpio, North Haledon, N.J.

[73] Assignee: Becton, Dickinson and Company, Paramus, N.J.

[21] Appl. No.: 864,388

[22] Filed: Dec. 27, 1977

[51] Int. Cl.² ............................................. A61B 5/14
[52] U.S. Cl. .................................. 128/766; 128/764; 137/512.1
[58] Field of Search ........... 128/2 F, 218 NV, 218 M, 128/274, 276, 350 V, DIG. 5, 762, 763, 764, 765, 766 (U.S. only); 137/512.1

[56] References Cited

U.S. PATENT DOCUMENTS

| 3,807,444 | 4/1974 | Fortune | 137/512.1 |
| 3,848,579 | 11/1974 | Villa-Real | 128/2 F |
| 3,938,513 | 2/1976 | Hargest | 128/218 NV X |
| 3,985,140 | 10/1976 | Harris | 128/350 V |
| 4,112,924 | 9/1978 | Ferrara et al. | 128/2 F |

FOREIGN PATENT DOCUMENTS

| 490050 | 1/1953 | Canada | 137/512.1 |
| 947170 | 1/1964 | United Kingdom | 137/512.1 |
| 497444 | 3/1976 | U.S.S.R. | 137/512.1 |

Primary Examiner—Richard T. Stouffer
Attorney, Agent, or Firm—Kane, Dalsimer, Kane, Sullivan and Kurucz

[57] ABSTRACT

A blood sampling device having two or more elastomeric one-way valves in parallel configuration. The valves prevent backflow towards the patient, but do not significantly decrease the blood flow from the patient. The valves may be arranged side-by-side within the device, or may alternatively be located one distally from the other.

3 Claims, 7 Drawing Figures

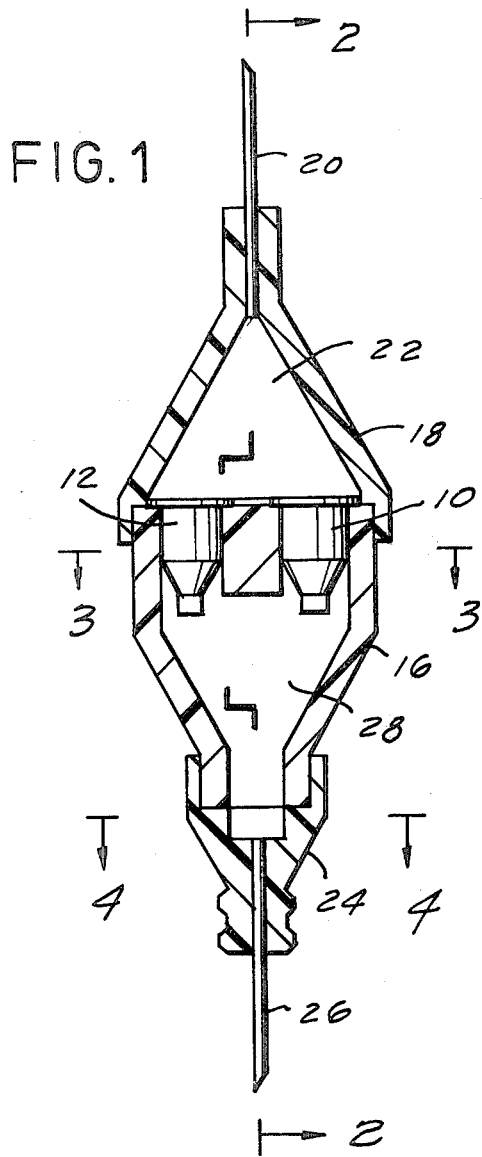
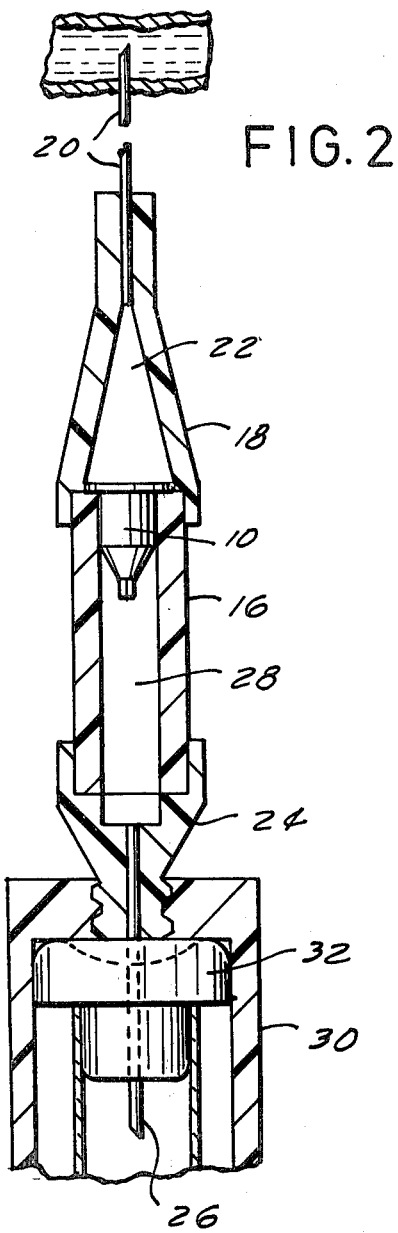
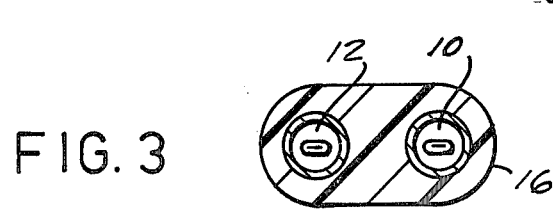
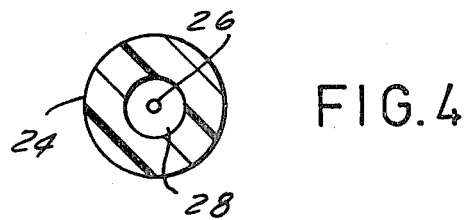

U.S. Patent  Jul. 15, 1980  Sheet 2 of 2  4,212,308
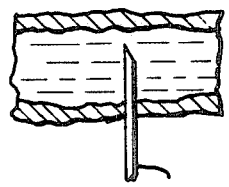
FIG. 5
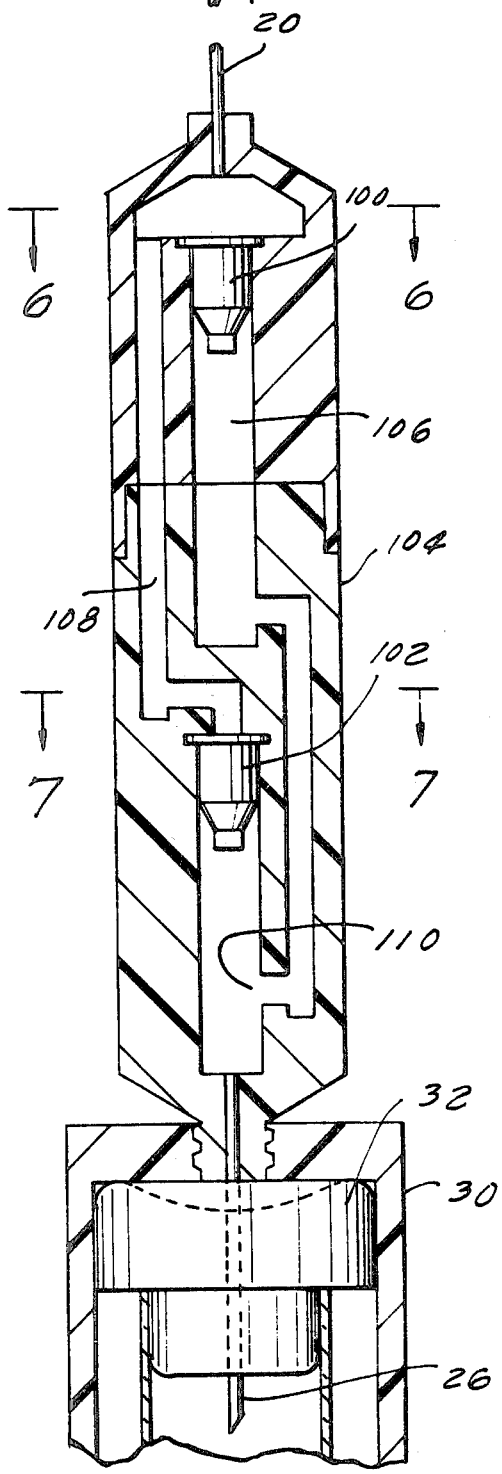
FIG. 6
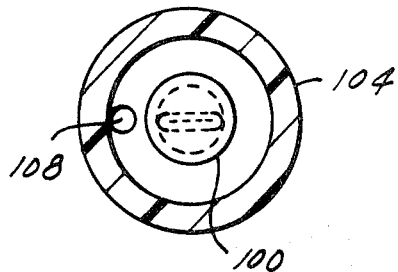
FIG. 7
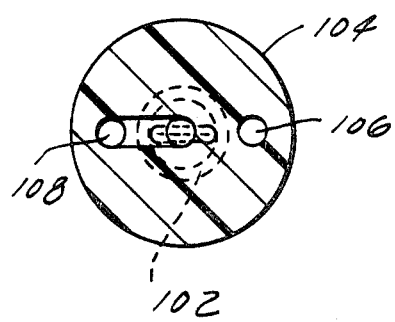

PARALLEL-FLOW ONE-WAY BLOOD SAMPLING DEVICE

BACKGROUND OF THE INVENTION

The field of the invention concerns devices for taking samples of body fluids such as blood, and in particular multiple sampling needles having one-way valve assemblies to prevent backflow.

One-way valves, such as those of elastomeric composition, are effective in preventing backflow, but it is often desirable to have the fluid collected at a higher rate. Elastomeric valves restrict fluid flow because of the restraint force caused by the elasticity which maintains such valves in a normally closed position.

In blood-sampling needle assemblies utilizing singular elastomeric valves, flow rate reductions (or fill time increases) can be 60% or higher as compared with the use of no valve at all. For this reason, medical personnel often prefer using the valveless assembly even though there is the risk of some backflow. Because the blood is commonly mixed with chemicals such as anticoagulants once it is withdrawn, there is the possibility of these chemicals entering the bloodstream.

Another problem associated with the use of blood-sampling devices having only one valve is that failure of the valve will result in no sample being withdrawn at all. This necessitates another injection of the patient, which is inconvenient for both the staff and the patient.

SUMMARY OF THE INVENTION

With the above background in mind, it is one of the primary objects of the invention to provide a multiple sampling needle assembly for the collection of blood or other body fluids which is both economical and efficient.

It is another object of the invention to provide a sampling device which allows the collection of body fluids at a faster rate than presently available devices, and which also prevents backflow.

Still another object of the invention is to reduce the possibility of failure of such a device due to the sticking of a valve.

These and other objects are accomplished by providing a needle assembly having a plurality of one-way valves arranged in parallel configuration. The device has a forward end adapted for penetration of a fluid vessel within the body, and a means for supplying negative pressure is provided for withdrawing the fluid towards the rear end. A Vacutainer tube is suitable for serving as both a collection container and the source of negative pressure. A plurality of valves, arranged in parallel configuration, are located between the forward end and the source of negative pressure. In this manner, flow into the collection container occurs at a higher rate than conventional devices employing only one valve. Futhermore, the failure of one valve does not prevent a sample from being taken, as flow will occur through the other valve or valves.

BRIEF DESCRIPTION OF THE DRAWINGS

FIG. 1 is a sectional elevational view of the device.

FIG. 2 is a sectional elevational view of the device shown in FIG. 1 as viewed from another side.

FIG. 3 is a cross-sectional view of the device taken along line 3—3 of FIG. 1.

FIG. 4 is a cross-sectional view of the device taken along line 4—4 of FIG. 1.

FIG. 5 is a partial sectional view of the body of another embodiment of the device wherein one valve is located distally from the other.

FIG. 6 is a cross-sectional view of the device shown in FIG. 5 taken along the line 6—6.

FIG. 7 is a cross-sectional view of the device taken along line 7—7 of FIG. 5.

DETAILED DESCRIPTION OF THE INVENTION

FIGS. 1-4 illustrate an embodiment of the invention which is both simple in construction and provides an acceptable flow rate. One-way duckbill valves 10 and 12, made from rubber or any other suitable elastomeric material, are mounted on surface 14 which is adapted for accommodation of said valves. The valves and mounting structure 14 are all contained within a housing assembly 16. A holder 18 is attached to the forward end of the housing 16, and an intravenous cannula 20 attached to the holder. Fluid communication between the cannula 20 and the valves is provided by means of chamber 22 which is located therebetween.

A second holder 24 is mounted to the opposite end of the housing 16, and a second cannula 26 is attached thereto. Fluid communication is provided between the downstream ends of the valves and the cannula 26 by means of a chamber 28. Whereas the needle 20 attached to holder 18 is used for penetration of one of the vessels of the body containing fluid, the other needle 26 is adapted for penetration of the resilient closure of an evacuated container.

The cross-sectional views of the device (FIGS. 3 and 4) show the valves to be located side by side. The housing 16 is accordingly elliptical in shape.

Another embodiment of the invention is shown in FIGS. 5-7. One-way valves 100 and 102 are arranged such that valve 102 is located distally from valve 100. A smaller housing 104 may thereby be utilized in the blood sampling apparatus, as evidenced in FIGS. 6 and 7. It is apparent from these figures that the valves are positioned along the longitudinal axis of the housing, as are the two cannulas.

Valve 100 is located within a first conduit 106, and valve 102 within a second conduit 108. The conduits must not be joined between the two valves or backflow would be short-circuited around the valves. The conduits are joined at a junction 110 where full flow is obtained.

The invention functions in the same manner as conventional multiple sampling needles, with the noted advantage of allowing a higher flow rate than the conventional devices. The intravenous needle is injected into a fluid-containing vessel of the body, such as a vein. After venipuncture has been accomplished, an evacuated tube 30 is positioned such that its resilient closure 32 is punctured by the cannula which extends away from the patient. Referring to FIG. 1, blood is drawn, respectively, through cannula 20, chamber 22, valves 10 and 12, chamber 28, cannula 26, and into the evacuated tube. A Vacutainer tube is well suited for use with the invention. The embodiment shown in FIGS. 5-7 operates in a similar manner.

In successful applications of the invention, considerable flow rate increases (up to 91%) have been found over conventional single-valve assemblies. More than two valves may be used in parallel to obtain further increases, but there are diminishing returns in such embodiments.

The above description and drawings are illustrative of specific embodiments of the invention, and other structures and uses of the parallel valve assembly will be readily apparent to those skilled in the art. The scope of the invention is not limited to the aforesaid embodiments, and should be interpreted in light of the appended claims.

What is claimed is:

1. A device for sampling a body fluid such as blood, comprising:

a housing having a forward end and a distal end;

a first cannula secured to the forward end of said housing for penetration of a fluid-containing vessel of a patient's body;

a second cannula secured to the distal end of said housing;

a first conduit within said housing, said conduit being in fluid communication with said first and second cannulas;

a first one-way valve mounted within said first conduit;

a second conduit within said housing, said second conduit being in fluid communication with said first and second cannulas; and a second one-way valve mounted within said second conduit, said first and second valves capable of independently and simultaneously permitting downstream flow therethrough towards said second cannula, said valves being aligned with each other along the longitudinal axis of said housing, one of said valves being mounted nearer the distal end of the housing than the other.

2. The invention as described in claim 1 wherein the valves are elastomeric.

3. The invention as described in claim 2 wherein the valves are duckbill check valves.

* * * * *